United States Patent [19]

Moreau et al.

[11] Patent Number: 5,663,295
[45] Date of Patent: Sep. 2, 1997

[54] OPIOID PEPTIDES

[75] Inventors: Jacques-Pierre Moreau, Upton; Sun Hyuk Kim, Needham; John E. Taylor, Upton, all of Mass.

[73] Assignee: Biomeasure Inc., Milford, Mass.

[21] Appl. No.: 352,391

[22] Filed: Dec. 8, 1994

Related U.S. Application Data

[63] Continuation-in-part of Ser. No. 974,943, Nov. 12, 1992, abandoned.

[51] Int. Cl.$^6$ .............................. A61K 38/00; C07K 7/00; C07K 7/06
[52] U.S. Cl. ............................ 530/330; 530/329
[58] Field of Search ...................... 530/330, 329; 514/17, 16, 18

[56] References Cited

U.S. PATENT DOCUMENTS

| | | | |
|---|---|---|---|
| 4,216,128 | 8/1980 | Sarantokis | 514/17 |
| 4,599,325 | 7/1986 | Hansen, Jr. et al. | 514/19 |

FOREIGN PATENT DOCUMENTS

| | | |
|---|---|---|
| 27 03 109 A1 | 8/1977 | Germany. |
| WO 87/06835 | 11/1987 | WIPO. |

OTHER PUBLICATIONS

Salvadori et al., "Synthesis and Pharmacological Activity of the N-terminal Dermorphin Tetrapeptide Analogs with CH$_2$-NH Peptide Bond Isosteres", Int. J. Peptide Protein Res. 40:437–444, 1992.

Kubota, et al, vol. 28, Chem. Pharm. Bull. vol. 28, 1980.

Coy et al., "Solid Phase Reductive Alkylation Techniques in Analogue Peptide Bond and Side Modification", Tetrahedron, 44:835–844, 1988.

Hruby et al., "Recent Developments in the Design of Receptor Specific Opioid Peptides" Medical Research Reviews 9:343–401, 1989.

Sasaki et al., "Studies on Analgesic Oligopeptides. VII. Solid Phase synthesis and Biological Properties of Tyr-D-Arg-Phe-βAla-NH2 & Its Fluorinated Aromatic Amino Acid Der . . . ", Chem. Pharm. Bull 39:2316–2318, 1991.

Vavrek et al., "Minimum Structure Opioids–Dipeptide and Tripeptide Analogs of the Erkephalins" Peptides 2:303–308, 1981.

Primary Examiner—Cecilia Tsang
Assistant Examiner—S. G. Marshall
Attorney, Agent, or Firm—Fish & Richardson P.C.; William E. McGowan

[57] ABSTRACT

Opioid peptides including those of the formula

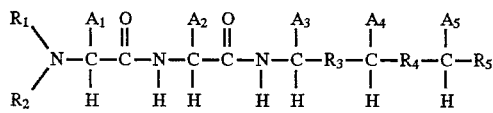

in which $A_1$ is the identifying group of an amino acid selected from 3,4-dihydroxyphenylalanine, 3,4-dimethoxyphenylalanine, azatyrosine, and 2,6-dimethyltyrosine; $A_2$ is the identifying group of an amino acid selected from D-Ala and D-Arg; $A_3$ is H, or the identifying group of an amino acid selected from of 3,4-dihydroxyphenylalanine and 3,4-dimethoxyphenylalanine, $A_4$ is H, cyclohexylmethyl, the identifying group of an amino acid selected from 3,4-dihydroxyphenylalanine, 3,4-dimethoxyphenylalanine, Phe, and substituted Phe with its benzene ring substituted by halogen, NO$_2$, OH, or CH$_3$; $A_5$ is the identifying group of a D- or L-amino acid selected from Leu, Nle, Lys, Met and Met(O), or is deleted together with R$_4$—CH attached thereto; each R$_1$ and R$_2$ is —H, —C(NH$_2$)=NH, or C$_{1-12}$ alkyl; R$_3$ is

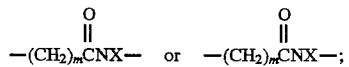

R$_4$ is

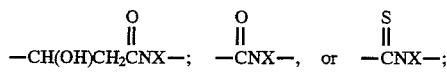

and R$_5$ is —(CH$_2$)$_{n+1}$OH,

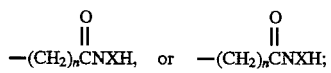

wherein m is 0-6, n is 0-6, and X is H, C$_{1-12}$ alkyl, C$_{6-12}$ aryl, C$_{7-18}$ aralkyl, C$_{7-18}$ alkaryl, C$_{7-18}$ alkayl, C$_{6-17}$ pyridylalkyl, or C$_{6-17}$ alkylpyridyl; provided that when one of R$_1$ and R$_2$ is —C(NH$_2$)=NH, the other must be H; or a pharmaceutically acceptable salt thereof.

4 Claims, No Drawings

OPIOID PEPTIDES

This application is a continuation-in-part of U.S. patent application Ser. No. 07/974,943, filed Nov. 12, 1992, now abandoned.

FIELD OF THE INVENTION

The present invention relates to short peptides. More particularly, it relates to short peptides capable of selectively binding to receptors on cells.

BACKGROUND OF THE INVENTION

Since the discovery of endogenous opioid peptides in the 1970's, extensive research in opioid chemistry and biology have suggested the existence of multiple opioid receptors: μ (mu), δ (delta) and κ (kappa).

The identification of multiple receptors is particularly interesting in that many opioids exert a variety of effects including analgesia, addiction, respiratory depression, inhibition of gut transit, and cardiotoxicity. See e.g., *The Pharmacological Basis of Therapeutics*, McMillan, pp. 496–536, New York (1980); Hruby et al., *Med. Res. Rev.* 9:343 (1989); and Zimmermann, et al., *J. Med. Chem.* 33:895 (1990).

Recent work has suggested that opioid peptides may also be involved in pathological states, including cancer. As shown in Table 1, multiple opioid receptors are present on numerous tumor cell lines.

While the exact role played by opioid peptides in oncogenic events remains unknown, opioids have been found to alter cell function and growth [Slotkin et al. *Life Sci.* 26:861 (1980); and Wilson et al. *J. Pharmacol. Exp. Ther.* 199:368 (1976)], to inhibit the growth of cultured neuroblastoma cells [Zagon et al. *Brain Res. Bull.* 7:25 (1981)], and to inhibit neuroblastoma tumor growth and prolong survival times, in an opioid antagonist sensitive manner, in mice with transplanted neuroblastomas, B-16 melanoma, MCF-7 breast cancer, human lung cancer cells and others [Zagon et al. *Life Sci.* 28:1095 (1981); Zagon et al. *Science* 221:671 (1983); and Von Hoff et al. *Proc., Am. Assoc. Cancer Res.*, Abstract 932, p. 236 (1982); Srisuchark et al. *Int. J. Immunopharm.* 11(5):487 (1989); Minna et al. *Proc. Natl. Acad. Sci.*, 87:3294 (1990); ibid. 89:1169 (1992)].

TABLE 1

Opiate Receptor Binding-Tumors or Tumor Cell Lines*

| Tumor | Opiate Receptor Subtype | Receptor Conc. (fmol/mg protein) |
|---|---|---|
| Inventors' Data | | |
| SCLC NCI-H69 | mu | 0 |
| SCLC NCI-H69 | delta | 23 |
| SCLC NCI-H69 | kappa | 0 |
| A549 NSCLC | mu | 0 |
| A549 NSCLC | delta | 0 |
| A549 NSCLC | kappa | 0 |
| MCF-7 | mu | 0 |
| MCF-7 | delta | 23 |
| MCF-7 | kappa | 0 |
| M 5123 Hepatoma | mu | 0 |
| B16 Melanoma | mu | 0 |
| B16 Melanoma | kappa | 129 |
| R3327 Prostate | mu | 0 |
| Data from Maneckjee et al. Proc. Natl. Acad. Sci. USA 87:3294 (1990) | | |
| SCLC NCI-H187 | nonselective | 450 |
| SCLC NCI-H69 | nonselective | 202 |
| SCLC NCI-H146 | nonselective | 172 |
| SCLC NCI-N417 | nonselective | 39 |
| SCLC NCI-H345 | nonselective | 18 |
| NSCLC NCI-H322 | nonselective | 293 |
| NSCLC NCI-H460 | nonselective | 194 |
| NSCLC NCI-H157 | nonselective | 157 |
| NSCLC NCl-H23 | nonselective | 119 |
| NSCLC NCI-H290 | nonselective | 78 |
| Data from Zagon et al. J. Natl. Cancer Inst. 79:1059 (1987) | | |
| Breast Adenocarcinoma | delta | 8.3 |
| Brent Adenocarcinoma | mu | 14.2 |
| Breast Adenocarcinoma | kappa | 10.0 |
| Overian Fibroma | delta | 225.0 |
| Overian Fibroma | kappa | 15.5 |
| Endometrial Adenocarcinoma | delta | 1.03 |
| Endometrial Adenocarcinoma | kappa | 30.2 |
| Rectal Adenocarcinoma | delta | 41.0 |
| Rectal Adenocarcinoma | kappa | 54.0 |

*does not exclude tumors expressing yet uncharacterized opiate receptor isotypes.

SUMMARY OF THE INVENTION

Structures and Abbreviations

AHPPA=(3S, 4S) -4-amino-3-hydroxy-5-phenyl-pentanoic acid

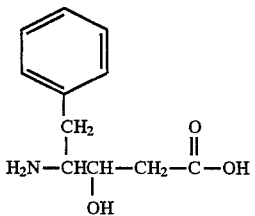

ACHPA=(3S, 4S)-4-amino-5-cyclohexyl-3-hydroxy-pentamoic acid

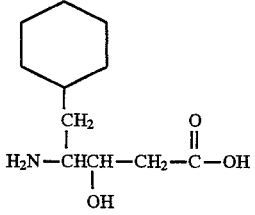

APP=(4R)-4-amino-5-phenylpentanoic acid

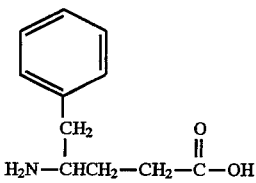

PEG=N-phenylethylglycine

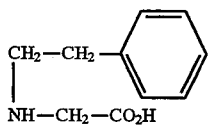

azatyrosine=L-3-(5-hydroxy-2-pyridyl)alanine

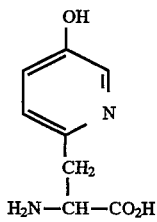

DOPA=3,4-dihydroxyphenylalanine

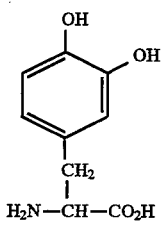

homophenylalanine

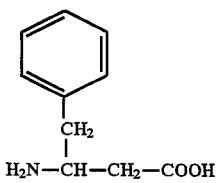

Nle=Norleucine
Met(O)=methionine sulfoxide

The present invention disclose a class of novel opioid peptides.

More specifically, one aspect of the invention relates to peptides of the formula:

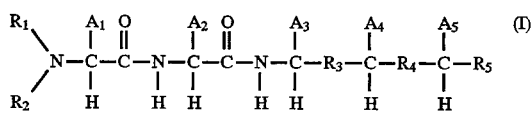

In which $A_1$ is the identifying group of an amino acid selected from 3,4-dihydroxyphenylalanine, 3,4-dimethoxyphenylalanine, azatyrosine, and 2,6-dimethyltyrosine;

$A_2$ is the identifying group of an amino acid selected from D-Ala and D-Arg;

$A_3$ is H, or the identifying group of an amino acid selected from of 3,4-dihydroxyphenylalanine and 3,4-dimethoxyphenylalanine, $A_4$ is H, cyclohexylmethyl, the identifying group of an amino acid selected from 3,4-dihydroxyphenylalanine, 3,4-dimethoxyphenylalanine, Phe, and substituted Phe with its benzene ring substituted by halogen, $NO_2$, OH, or $CH_3$;

$A_5$ is the identifying group of a D- or L-amino acid selected from Leu, Nle, Lys, Met and Met(O), or is deleted together with $R_4$—CH attached thereto;

each $R_1$ and $R_2$ is —H, —$C(NH_2)$=NH, or $C_{1-12}$ alkyl; $R_3$ is

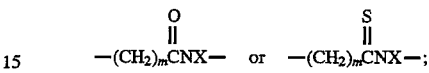

$R_4$ is

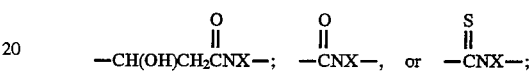

and
$R_5$ is —$(CH_2)_{n+1}OH$,

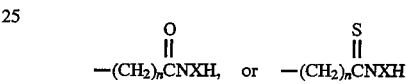

(m is 0–6, n is 0–6, and X is H, $C_{1-12}$ alkyl, $C_{6-12}$ aryl, $C_{7-18}$ aralkyl, $C_{7-18}$ alkaryl, $C_{7-18}$ alkaryl, $C_{6-17}$ pyridylalkyl, or $C_{6-17}$ alkylpyridyl); provided that when one of $R_1$ and $R_2$ is —$C(NH_2)$=NH, the other must be H.

Preferably, $A_1$ is the identifying group of an amino acid selected from 3,4-dihydroxyphenylalanine and 3,4-dimethoxyphenylalanine; $A_5$ is the identifying group of a D- or L-amino acid selected from Leu, Met and Met(O), or is deleted together with $R_4$—CH attached thereto; each $R_1$ and $R_2$ is —H or —$C(NH_2)$=NH; $R_3$ is

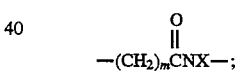

$R_4$ is

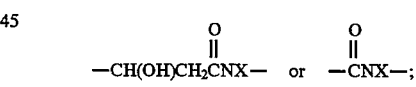

$R_5$ is —$(CH_2)_{n+1}OH$ or

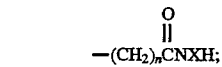

m is 0–2; n is 0–2; and X is H, $C_{1-12}$ alkyl, or $C_{7-18}$ aralkyl.

Another aspect of the invention relates to peptides of formula (I), in which $A_1$ is the identifying group of an amino acid selected from 3,4-dihydroxyphenylalanine, 3,4-dimethoxyphenylalanine, azatyrosine, Tyr, and 2,6-dimethyltyrosine;

$A_2$ is the identifying group of an amino acid selected from D-Ala and D-Arg;

$A_3$ is H or the identifying group of an amino acid selected from 3,4-dihydroxyphenylalanine and 3,4-dimethoxyphenylalanine;

$A_4$ is H, cyclohexylmethyl, or the identifying group of an amino acid selected from 3,4-dihydroxyphenylalanine and 3,4-dimethoxyphenylalanine;

$A_5$ is the identifying group of a D- or L-amino acid selected from Leu, Nle, Lys, Met and Met(O), or is deleted together with $R_4$—CH attached thereto;

each $R_1$ and $R_2$ is —H, —C(NH$_2$)=NH, or $C_{1-12}$ alkyl; $R_3$ is

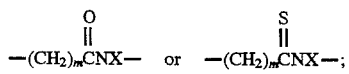

$R_4$ is

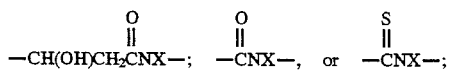

and $R_5$ is —(CH$_2$)$_{n+1}$OH,

(m is 0–6, n is 0–6, and X is H, $C_{1-12}$ alkyl, $C_{6-12}$ aryl, $C_{7-18}$ aralkyl, $C_{7-18}$ alkaryl, $C_{6-17}$ pyridylalkyl, or $C_{6-17}$ alkylpyridyl); provided that when one of $R_1$ and $R_2$ is —C(NH$_2$)=NH, the other must be H.

Preferably, $A_1$ is the identifying group of an amino acid selected from 3,4-dihydroxyphenylalanine, 3,4-dimethoxyphenylalanine, and Tyr; $A_5$ is the identifying group of a D- or L-amino acid selected from Leu, Met and Met(O), or is deleted together with $R_4$—CH attached thereto; each $R_1$ and $R_2$ is —H or —C(NH$_2$)=NH; $R_3$ is

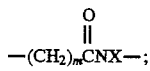

$R_4$ is

$R_5$ is —(CH$_2$)$_{n+1}$OH or

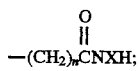

m is 0–2; n is 0–2; and X is H, $C_{1-12}$ alkyl, or $C_{7-18}$ aralkyl.

A further aspect of the invention relates to peptides of formula (I), in which $A_1$ is the identifying group of an amino acid selected from 3,4-dihydroxyphenylalanine, 3,4-dimethoxyphenylalanine, azatyrosine, Tyr, and 2,6-dimethyltyrosine;

$A_2$ is the identifying group of an amino acid selected from D-Ala and D-Arg;

$A_3$ is H or the identifying group of an amino acid selected from 3,4-dihydroxyphenylalanine and 3,4-dimethoxyphenylalanine;

$A_4$ is the identifying group of an amino acid selected from Phe, and substituted Phe with its benzene ring substituted by halogen, NO$_2$, OH, or CH$_3$;

$A_5$ is the identifying group of a D- or L-amino acid selected from Leu, Nle, Lys, Met and Met(O), or is deleted together with $R_4$—CH attached thereto;

each $R_1$ and $R_2$ is —H, —C(NH$_2$)=NH, or $C_{1-12}$ alkyl; $R_3$ is

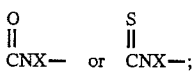

$R_4$ is

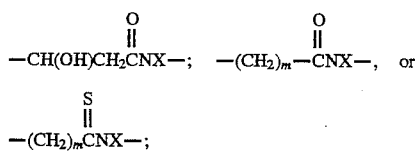

and $R_5$ is —(CH$_2$)$_{n+1}$OH,

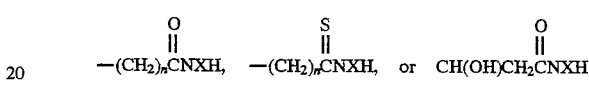

(m is 1–6, n is 0–6, and X is H, $C_{1-12}$ alkyl, $C_{6-12}$ aryl, $C_{7-18}$ aralkyl, $C_{7-18}$ alkaryl, $C_{7-18}$ alkaryl, $C_{6-17}$ pyridylalkyl, or $C_{6-17}$ alkylpyridyl); provided that when one of $R_1$ and $R_2$ is —C(NH$_2$)=NH, the other must be H.

Preferably, $A_1$ is the identifying group of an amino acid selected from 3,4-dihydroxyphenylalanine, 3,4-dimethoxyphenylalanine, and Tyr; $A_5$ is the identifying group of a D- or L-amino acid selected from Leu, Met and Met(O), or is deleted together with $R_4$—CH attached thereto; each $R_1$ and $R_2$ is —H or —C(NH$_2$)=NH; $R_3$ is

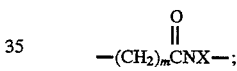

$R_4$ is

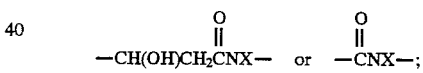

$R_5$ is —(CH$_2$)$_{n+1}$OH or

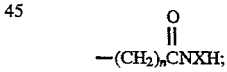

m is 1–2; n is 0–2; and X is H, $C_{1-12}$ alkyl, or $C_{7-18}$ aralkyl.

The present invention also covers peptides of formula (I), in which $A_1$ is the identifying group of an amino acid selected from 3,4-dihydroxyphenylalanine, 3,4-dimethoxyphenylalanine, azatyrosine, Tyr, and 2,6-dimethyltyrosine;

$A_2$ is the identifying group of an amino acid selected from D-Ala and D-Arg;

$A_3$ is H or the identifying group of an amino acid selected from 3,4-dihydroxyphenylalanine and 3,4-dimethoxyphenylalanine;

$A_4$ is H, cyclohexylmethyl, the identifying group of an amino acid selected from 3,4-dihydroxyphenylalanine, 3,4-dimethoxyphenylalanine, Phe, and substituted Phe with its benzene ring substituted by halogen, NO$_2$, OH, or CH$_3$;

$A_5$ is the identifying group of a D- or L-amino acid selected from Leu, Nle, Lys, Met and Met(O), or is deleted together with $R_4$—CH attached thereto;

each $R_1$ and $R_2$ is —H, —C(NH$_2$)=NH, or $C_{1-12}$ alkyl;

$R_3$ is —$CH_2NH$— or —CO•NH—;
$R_4$ is —$CH_2NH$— or —CO•NH—; and
$R_5$ is —$(CH_2)_{n+1}OH$,

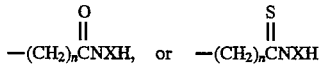

(n is 0–6, and X is H, $C_{1-12}$ alkyl, $C_{6-12}$ aryl, $C_{7-18}$ aralkyl, $C_{7-18}$ alkaryl, $C_{7-18}$ alkaryl, $C_{6-17}$ pyridylalkyl, or $C_{6-17}$ alkylpyridyl); provided that: when one of $R_1$ and $R_2$ is —$C(NH_2)$=NH, the other must be H; and one and only one of $R_3$ and $R_4$ is —$CH_2NH$—.

Preferably, $A_1$ is the identifying group of an amino acid selected from 3,4-dihydroxyphenylalanine, 3,4-dimethoxyphenylalanine, and Tyr; $A_5$ is the identifying group of a D- or L-amino acid selected from Leu, Met and Met(O), or is deleted together with $R_4$—CH attached thereto; each $R_1$ and $R_2$ is —H or —$C(NH_2)$=NH; $R_5$ is —$(CH_2)_{n+1}OH$ or

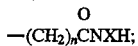

n is 0–2; and X is H, $C_{1-12}$ alkyl, or $C_{7-18}$ aralkyl. It is particularly preferred that $A_4$ be the identifying group of an amino acid selected from 3,4-dihydroxyphenylalanine and 3,4-dimethoxyphenylalanine.

Also within the invention are peptides of the formula:

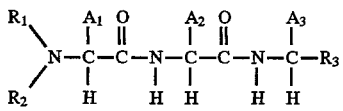

in which $A_1$ is the identifying group of an amino acid selected from 3,4-dihydroxyphenylalanine, 3,4-dimethoxyphenylalanine, azatyrosine, Tyr, and 2,6-dimethyltyrosine;

$A_2$ is the identifying group of an amino acid selected from D-Ala and D-Arg;

$A_3$ is the identifying group of an amino acid selected from 3,4-dihydroxyphenylalanine and 3,4-dimethoxyphenylalanine, or is deleted together with CO—NH—CH attached thereto;

each $R_1$ and $R_2$ is —H, —$C(NH_2)$=NH, or $C_{1-12}$ alkyl;
$R_3$ is —$(CH_2)_{n+1}OH$,

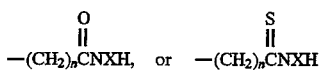

(n is 0–6; and X is H, $C_{1-12}$ alkyl, $C_{6-12}$ aryl, $C_{7-18}$ aralkyl, $C_{7-18}$ alkaryl, $C_{7-18}$ 3,4-dihydroxyphenylalkyl, $C_{7-18}$ 3,4-dimethoxyphenylalkyl, $C_{6-17}$ pyridylalkyl, or $C_{6-17}$ alkylpyridyl).

Preferably, $A_1$ is the identifying group of an amino acid selected from 3,4-dihydroxyphenylalanine, 3,4-dimethoxyphenylalanine, and Tyr; each $R_1$ and $R_2$ is —H or —$C(NH_2)$=NH; $R_3$ is

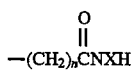

(X is H, $C_{1-12}$ alkyl, or $C_{7-18}$ aralkyl). It is particularly preferred that $A_3$ be deleted together with CO—NH—CH attached thereto.

Illustrative and non-limiting examples of peptides of the present invention are provided below:

DOPA-D-alanyl-glycyl-phenylalanyl-methionine amide,
DOPA-D-alanyl-glycyl-phenylalanyl methioninol,
DOPA-D-arginyl-glycyl-phenylalanyl-methionine amide,
DOPA-D-arginyl-glycyl-phenylalanyl methioninol,
3,4-dimethoxyphenylalanyl-D-alanyl-glycyl-phenylalanylmethionine amide,
3,4-dimethoxyphenylalanyl-D-alanyl-glycyl-phenylalanyl methioninol,
3,4-dimethoxyphenylalanyl-D-arginyl-glycyl-phenylalanylmethionine amide,
3,4-dimethoxyphenylalanyl-D-arginyl-glycyl-phenylalanylmethionine,
DOPA-D-alanyl-DOPA-β-alanine amide,
DOPA-D-arginyl-DOPA-β-alanine amide,
DOPA-D-alanyl-DOPA-β-alaninol,
DOPA-D-arginyl-DOPA-β-alaninol,
3,4-dimethoxyphenylalanyl-D-alanyl-DOPA-β-alanine amide,
3,4-dimethoxyphenylalanyl-D-arginyl-DOPA-β-alanine amide,
3,4-dimethoxyphenylalanyl-D-alanyl-DOPA-β-alaninol,
3,4-dimethoxyphenylalanyl-D-arginyl-DOPA-β-alaninol,
DOPA-D-alanyl-glycyl-PEG amide,
DOPA-D-arginyl-glycyl-PEG amide,
DOPA-D-alanyl-glycyl-APP amide,
DOPA-D-arginyl-glycyl-APP amide,
tyrosyl-D-alanyl-glycyl-PEG-methionine amide,
tyrosyl-D-arginal-glycyl-PEG-methionine amide,
tyrosyl-D-alanyl-glycyl-PEG methioninol,
tyrosyl-D-arginyl-glycyl-PEG methioninol,
tyrosyl-D-alanyl-glycyl-ACHPA amide,
tyrosyl-D-arginyl-glycyl-ACHPA amide,
tyrosyl-D-alanyl-glycyl-PEG amide,
tyrosyl-D-arginyl-glycyl-PEG amide,
tyrosyl-D-alanyl-DOPA-ACHPA amide,
tyrosyl-D-arginyl-DOPA-ACHPA amide,
tyrosyl-D-alanyl-DOPA-PEG amide,
tyrosyl-D-arginyl-DOPA-PEG amide,
tyrosyl-D-alanyl-3,4-dimethoxyphenylalanyl-ACHPA amide,
tyrosyl-D-arginyl-3,4-dimethoxyphenylalanyl-ACHPA amide,
tyrosyl-D-alanyl-3,4-dimethoxyphenylalanyl-PEG amide,
tyrosyl-D-arginyl-3,4-dimethoxyphenylalanyl-PEG amide,
amidinotyrosyl-D-alanyl-glycyl-PEG amide,
amidinotyrosyl-D-arginyl-glycyl-PEG amide,
tyrosyl-D-alanyl-DOPA-β-alanine amide,
tyrosyl-D-arginyl-DOPA-β-alanine amide,
tyrosyl-D-alanyl-DOPA-β-alaninol,
tyrosyl-D-arginyl-DOPA-β-alaninol,
tyrosyl-D-alanyl-DOPA-glycinol,
tyrosyl-D-arginyl-DOPA-glycinol,
tyrosyl-D-alanyl-glycyl-DOPA amide,
tyrosyl-D-arginyl-glycyl-DOPA amide,
tyrosyl-D-alanyl-3,4-dimethoxyphenylalanyl-β-alanine amide,
tyrosyl-D-arginyl-3,4-dimethoxyphenylalanyl-β-alanine amide,
tyrosyl-D-alanyl-3,4-dimethoxyphenylalanyl-β-alaninol,
tyrosyl-D-arginyl-3,4-dimethoxyphenylalanyl-β-alaninol,
tyrosyl-D-alanyl-glycyl-3,4-dimethoxyphenylalanyl amide,
tyrosyl-D-arginyl-glycyl-3,4-dimethoxyphenylalanyl amide,
tyrosyl-D-alanyl-glycyl-APP-methionine amide,
tyrosyl-D-alanyl-glycyl-APP methioninol,
tyrosyl-D-arginyl-glycyl-APP-methionine amide,
tyrosyl-D-arginyl-glycyl-APP methioninol,
tyrosyl-D-alanyl-glycyl-homophenylalanyl-methionine amide, tyrosyl-D-alanyl-glycyl-homophenylalanyl methioninol,
tyrosyl-D-arginyl-glycyl-homophenylalanyl-methionine amide,
tyrosyl-D-arginyl-glycyl-homophenylalanyl methioninol,
tyrosyl-D-alanyl-glycyl-AHPPA amide,
tyrosyl-D-arginyl-glycyl-AHPPA amide,
tyrosyl-D-alanyl-glycyl-APP amide,
tyrosyl-D-arginyl-glycyl-APP amide,
tyrosyl-D-alanyl-glycyl-homophenylalanine amide,
tyrosyl-D-arginyl-glycyl-homophenylalanine amide,
tyrosyl-D-alanyl-DOPA-AHPPA amide
tyrosyl-D-arginyl-DOPA-AHPPA amide
tyrosyl-D-alanyl-DOPA-APP amide
tyrosyl-D-arginyl-DOPA-APP amide
tyrosyl-D-alanyl-DOPA-homophenylalanine amide,
tyrosyl-D-arginyl-DOPA-homophenylalanine amide,
tyrosyl-D-alanyl-3,4-dimethoxyphenylalanyl-AHPPA amide,
tyrosyl-D-arginyl-3,4-dimethoxyphenylalanyl-AHPPA amide,
tyrosyl-D-alanyl-3,4-dimethoxyphenylalanyl-APP amide,
tyrosyl-D-arginyl-3,4-dimethoxyphenylalanyl-APP amide,
tyrosyl-D-alanyl-3,4-dimethoxyphenylalanyl-homophenylalanine amide,
tyrosyl-D-arginyl-3,4-dimethoxyphenylalanyl-homophenylalanine amide,
tyrosyl-D-alanyl-glycyl-ψ(CH$_2$NH)-phenylalanine ethylamide,
tyrosyl-D-alanyl-glycyl-ψ(CH$_2$NH)-phenylalanine propylamide,
tyrosyl-D-arginyl-glycyl-ψ(CH$_2$NH)-phenylalanine ethylamide,
tyrosyl-D-arginyl-glycyl-ψ(CH$_2$NH)-phenylalanine propylamide,
amidinotyrosyl-D-alanyl-glycyl-ψ(CH$_2$NH)-phenylalanine ethylamide,
amidinotyrosyl-D-alanyl-glycyl-ψ(CH$_2$NH)-phenylalanine propylamide,
amidinotyrosyl-D-arginyl-glycyl-ψ(CH$_2$NH)-phenylalanine ethylamide,
amidinotyrosyl-D-arginyl-glycyl-ψ(CH$_2$NH)-phenylalanine propylamide,
tyrosyl-D-arginal-glycyl-phenylalanyl-ψ(CH$_2$NH)-leucine amide,
tyrosyl-D-alanyl-DOPA-ψ(CH$_2$NH)-phenylalanine ethylamide,
tyrosyl-D-alanyl-DOPA-ψ(CH$_2$NH)-phenylalanine propylamide,
tyrosyl-D-arginyl-DOPA-ψ(CH$_2$NH)-phenylalanine ethylamide,
tyrosyl-D-arginyl-DOPA-ψ(CH$_2$NH)-phenylalanine propylamide,
amidinotyrosyl-D-alanyl-DOPA-ψ(CH$_2$NH)-phenylalanine ethylamide,
amidinotyrosyl-D-alanyl-DOPA-ψ(CH$_2$NH)-phenylalanine propylamide,
amidinotyrosyl-D-arginyl-DOPA-ψ(CH$_2$NH)-phenylalanine ethylamide,
amidinotyrosyl-D-arginyl-DOPA-ψ(CH$_2$NH)-phenylalanine propylamide,
tyrosyl-D-arginal-DOPA-Phenylalanyl-ψ(CH$_2$NH)-leucine amide,
tyrosyl-D-alanyl-3,4-dimethoxyphenylalanyl-ψ(CH$_2$NH)-phenylalanine ethylamide,
tyrosyl-D-alanyl-3,4-dimethoxyphenylalanyl-ψ(CH$_2$NH)-phenylalanine propylamide,
tyrosyl-D-arginyl-3,4-dimethoxyphenylalanyl-ψ(CH$_2$NH)-phenylalanine ethylamide,
tyrosyl-D-arginyl-3,4-dimethoxyphenylalanyl-ψ(CH$_2$NH)-phenylalanine propylamide,
amidinotyrosyl-D-alanyl-3,4-dimethoxyphenylalanyl-ψ(CH$_2$NH)-phenylalanine ethylamide,
amidinotyrosyl-D-alanyl-3,4-dimethoxyphenylalanyl-ψ(CH$_2$NH)-phenylalanine propylamide,
amidinotyrosyl-D-arginyl-3,4-dimethoxyphenylalanyl-ψ(CH$_2$NH)-phenylalanine ethylamide,
amidinotyrosyl-D-arginyl-3,4-dimethoxyphenylalanyl-ψ(CH$_2$NH)-phenylalanine propylamide,
tyrosyl-D-arginal-3,4-dimethoxyphenylalanyl-phenylalanyl-ψ(CH$_2$NH)-leucine amide,
tyrosyl-D-alanyl-DOPA amide,
tyrosyl-D-arginyl-DOPA amide,
tyrosyl-D-alanyl-3,4-dimethoxyphenylalanine amide,
tyrosyl-D-arginyl-3,4-dimethoxyphenylalanine amide,
tyrosyl-D-alanine 3-(3',4'-dihydroxyphenylpropyl)amide,
tyrosyl-D-arginine 3-(3',4'-dihydroxyphenylpropyl)amide,
tyrosyl-D-alanine 3-(3',4'-dimethoxyphenylpropyl)amide,
tyrosyl-D-arginine 3-(3',4'-dimethoxyphenylpropyl)amide,
DOPA-D-alanine 3-phenylpropylamide,
DOPA-D-alanine 2-(2-aminoethylpyridyl)amide, and
DOPA-D-arginine 2-(2-aminoethylpyridyl)amide.

In this disclosure, the identifying group of an α-amino acid is the atom or group of atoms bound to the asymmetric α-carbon atom, other than the carbonyl carbon atom, the amino nitrogen atom and the H atom. To illustrate by examples, the identifying group of alanine is —CH$_3$ and the identifying group of phenylalanine is (C$_6$H$_5$)CH$_2$—.

Also, unless specified as an L- or D-isomer, an amino acid is intended to be an L amino acid.

Further, a short line between two amino acid residues (e.g., DOPA-D-alanine 3-phenylpropylamide) represents a peptide bond; that is, a covalent bond between C of a carbonyl group and N of an amino group. The symbol ψ indicates the presence of a non-peptide bond and the nature of the non-peptide bond is described in the parentheses following ψ (e.g., tyrosyl-D-alanyl-glycyl-ψ(CH$_2$NH)-phenylalanine ethylamide). Thus, —ψ(CH$_2$NH)— represents the presence of a bond between two amino acid residues in which the carbon atom participating in the bond is reduced from a carbonyl carbon to a methylene carbon.

A detailed discussion of the chemistry of non-peptide bonds is given in Coy et al. *Tetrahedron* 44:835 (1988); Tourwe *Janssen Chim. Acta* 3:3–15, 17–18 (1985); and Spatola in *Chemistry and Biochemistry of Amino Acids, Peptides and Proteins* (B. Weinstein, ed.), M. Dekker, New York and Basal, pp. 267–357 (1983). All of them are hereby incorporated by reference.

Pharmaceutically acceptable salts of the above-described peptides are also within the present invention. Examples of preferred salts include those formed with therapeutically acceptable acids, e.g., hydrochloric, hydrobromic, sulfuric, nitric, phosphoric, citric, acetic, maleic, lactic, malic, ascorbic succinic, benzoic, fumaric, salcyclic, methanesulfonic, trifluoroacetic, toluenesulfonic, or pamoic acid, as well as polymeric acids such as tannic acid or carboxymethyl cellulose, lactate/glycolate.

Opioid peptides are known to possess analgesic, antitussive, and antidiarrheal activity and thus may be used in human or veterinary medicine for the relief or prevention of pain, for the treatment of diarrhea or dysentery, for the suppression of cough and for hypertension. Further, the opioid peptides of the invention are effective in treating various cancers (e.g., lung, breast, melanoma, or neuroblastoma).

A therapeutically effective amount of a peptide of the invention and a pharmaceutically acceptable carrier substance (e.g., magnesium carbonate or lactose) can be formulated to form a therapeutic composition, such as (i) a pill, tablet, capsule, or liquid for oral administration to a patient; (ii) a liquid or an ointment capable of being administered by inhalation, transdermally, nasally, rectally or sublingually; (iii) a liquid capable of being administered intravenously, parenterally, subcutaneously or intraperitoneally; or (iv) an oral or a parenteral sustained release formulation. Thus, the opioid peptide of the invention may be administered to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes. The peptides can be administered to a human patient in a dosage of 1000 µg/kg/day to 50 mg/kg/day.

The peptides of the present invention can also be used as tools for detecting specific opioid receptors in cells of certain tissues or organs.

Other features and advantages of the invention will be apparent from the following description of the preferred embodiments thereof, and from the claims.

DESCRIPTION OF THE PREFERRED EMBODIMENTS

Synthesis

The peptides of this invention can be readily prepared by standard solution or solid phase peptide synthesis. Thus, procedures analogous to those disclosed in *Solid Phase Peptide Synthesis* by Stewart and Young, Pierce Co., Illinois, 1984 or *Principles of Peptide Synthesis* by Springer-Verlag, Berlin, 1984 may be followed. Both of them are hereby incorporated by reference.

Peptides of the invention that contain a $CH_2NH$ non-peptide bond can be prepared by reacting on N-protected amino acid aldehyde with the free amino group of another C-protected amino acid using $NaCNBH_3$, as described in Martinez et al. *J. Med. Chem.* 28:1874 (1985) and Coy et al. *Tetrahedron* 44:835 (1988), both of which are hereby incorporated by reference.

AHPPA and ACHPA can be synthesized according to the method of Hui et al. *J. Med. Chem.* 30:1281 (1987); Schuda et al., 1987, *J. Org. Chem.* 53:873; and Rich et al., 1988, *J. Org. Chem.* 53:869. All three of them are hereby incorporated by reference.

To obtain N-terminal amidinotyrosyl peptides, the peptide salt (e.g., an acetates or trifluoroacetate salt) was reacted with 3,5-dimethylpyrazolo-1-carboxamidine nitrate in the presence of base, e.g. triethylamine, diisopropylamine, or aqueous NaOH (pH 9.3–9.5), in inert solvents, e.g. alcohol, water, tetrahydrohuran or its mixture, at 0°–80° C., 2 hours to several days. The intermediates and final products were isolated and purified by standard methods, e.g., by column chromatography, crystallization on high performance liquid chromatography ("HPLC"). Purity was determined using chromatographic, spectroscopic and chemical analysis.

Benzyloxycarbonyl ("CBZ")-tyrosyl-D-alanyl-glycyl-PEG glycine amide was synthesized as follows. 2.3 ml diisopropylamine was added to a mixture of CBZ-tyrosyl-D-alanine (1.65 g), glycyl-PEG amide trifluoroacetic acid salt (1.5 g) and BOP reagent (i.e., benzotriazol-1-yloxytris (dimethylamine)phosphonium hexafluorophosphate) (2.1 g) in 20 ml dimethylformamide ("DMF") and the mixture was stirred at room temperature overnight. Solvent was removed in vacuo to a dryness and the residue partitioned between ethylacetate and water. The organic layer and any partially insoluble solids were combined, the solvent evaporated, and the residue recrystallized from ethylacetate. Yield: 0.65 g; Thin layer chromatography ("TLC") (Silica gel: $CHCl_3$/MeOH 9:1, Rf 0.37).

CBZ-tyrosyl-D-alanyl-glycyl-PEG amide (0.6 g) in 20 ml methanol was hydrogenated under 32 psi using 100 mg 10% Pd-C for 4 hours. The mixture was then filtered through celite pad, washed with alcohol. Thereafter, the filtrate was concentrated in vacuo to dryness. Yield: 0.49 g colorless solid; TLC (silica gel; $CHCl_3$/MeOH=4:1, Rf 0.1). Synthetic amino acids are commercially available.

(4R)-Boc-amino-5-phenyl-pentanoic acid was synthesized as follows. To a partial solution of Boc-phenylalanine aldehyde (2.3 g) in 30 ml dichloromethane cooled to 0°–5° C., was added carbethoxymethylene triphenylphosphorane (10 g). The mixture was stirred at 0°–5° C. for 3 hours then room temperature overnight. Solvent was evaporated in vacuo to a dryness and the residue was triturated with boiling ether (~200 ml). Ether extract was concentrated in vacuo and the residue was chromatographed on silica gel (50 g) using hexane/ethylacetate (5:1) as eluants. Appropriate fractions were pooled and solvents removed in vacuo to a dryness. Yield: 2.1 g; TLC (Silica gel: hexane/ethylacetate= 2:1, Rf 0.57). The product was then dissolved in 20 µl EtOH to which 150 mg of 10% Pd-C was added. Hydrogenation was carried out under 30 psi for 5½ hours. The mixture was filtered through celite pad, washed with alcohol and the filtrate was concentrated in vacuo to a dryness. Yield: 2.1 g colorless solid. 1.4 g of the colorless solid was suspended in 20 ml methanol and, upon addition of 6 ml 2N-NaOH, stirred at room temperature for 1 hour. After evaporation of solvent, aqueous layer was acidified to pH 2–3, extracted with ethylacetate, and dried ($MgSO_4$). Solvent was evaporated in vacuo to a dryness. Yield: 1.23 g colorless solid; TLC (Silica gel: $CHCl_3$/MeOH/HoAC 9:1:0.1, Rf 0.62).

Tyrosyl-D-alanyl-glycyl-AHPPA amide was synthesized as follows. Boc-AHPPA was first incorporated on 4-methylbenzhydrylamine resin. 1.0 g (0.64 mmole) 4-methylbenzhydrylamine-polystyrene resin (Bachem, Inc.) in the chloride ion form was placed in the reaction vessel of an Advanced ChemTech 200 peptide synthesizer programmed to perform the following reaction cycle: (a) methylene chloride; (b) 10% triethylamine in chloroform; (c) methylene chloride; and (d) dimethylformamide. The neutralized resin was mixed for 18 hours with the preformed active ester made from Boc AHPPA (1.92 mmole), diisopropyl carbodiimide (1.92 mmole), and hydroxybenzotriazole hydrate (1.92 mmole) in dimethylformamide in an ice bath for 1 hour. The resulting amino acid resin was washed on the synthesizer with dimethylformamide followed by methylene chloride. Acetylation of any free amino group of the resin was performed by mixing the amino acid resin for 15 minutes with N-acetyl imidazole (5 mmole) in methylene chloride.

The remaining amino acids were coupled as follows. The peptide synthesizer was programmed to perform the following reaction cycle: (a) methylene chloride; (b) 33% trifluoroacetic acid ("TFA") in methylene chloride 2 times (5 min. and 25 min. each); (c) methylene chloride; (d) isopropyl alcohol; (e) 10% triethylamine in chloroform; and (f) methylene chloride. The following amino acid (e.g. Boc-glycine) and diisopropyl carbodiimide (3 eq. each) in methylene chloride were mixed for 2 hours and the resulting amino acid resin was then cycled through steps (a) to (f) in the above procedure. The next following Boc-amino acids (Boc-D-alanine, Boc-tyrosine) (3 eq. each) were coupled successively following the same procedure. After drying, the resin (1.3 g) was mixed with anisole (5 ml), dithiothreitol (200 mg) and anhydrous hydrogen fluoride (35 ml) at 0° C. for 45 minutes. Excess hydrogen fluoride was evaporated rapidly under a stream of dry nitrogen and the free peptide was precipitated and washed with ether. The crude peptide was then dissolved in a minimum volume of 1M acetic acid and applied to Vydac C18 column (2.54 cm I.D.×35 cm). The peptide was eluted with a gradient (20%–80%) of 50/50 0.1% trifluoroacetic acid/acetonitrile in 0.1% trifluoroacetic acid in water. Fractions were examined by analytical HPLC. Most of the solvent was removed in vacuo to yield a small volume, and thereafter the product lyophilized. Yield: 24 mg colorless solid.

Tyrosyl-D-arginyl-glycyl-phenylalanyl-ψ($CH_2NH$)-leucine amide was synthesized as follows. The procedure is essentially as described above except for the following reductive alkylation step. Boc-phenylalanine aldehyde (2.5 eq), prepared by the method of Pehrentz and Castro, *Synthesis*, p. 676 (1983), hereby incorporated by reference, was first dissolved in 5 ml of dry DMF and then added to the suspension of TFA salt of leucine resin in DMF containing 1% acetic acid, followed by the portion-wise addition of sodium cyanoborohydride (4 eq) over 40 minutes. After stirring for 1 hour, the resin mixture was found to be negative to ninhydrin reaction.

Other compounds can be prepared in one or more of the manners described above and screened for effectiveness following procedures set forth below. Both the synthetic and screening methods are well known to a person of ordinary skill in the art.

Activity (1) In vitro inhibition of radioligand to opioid receptors

The ability of various opioid peptides of the present invention to selectively inhibit binding of μ receptor ligand to μ receptor is shown in Table 2.

TABLE 2

IN VITRO RECEPTOR BINDING-Ki (nM)

| CODE | μ RECEPTOR DAGO | δ RECEPTOR DPPE | κ RECEPTOR U69,593 |
| --- | --- | --- | --- |
| BIM-38052 | 0.19 ± 0.03 | 27.17 ± 3.23 | 241.67 ± 10.93 |
| BIM-38031 | 0.65 ± 0.05 | 12.60 ± 2.52 | 205.00 |
| BIM-38020 | 1.18 ± 0.09 | 1014.00 ± 420.00 | 319.75 ± 9.92 |
| BIM-38007 | 1.36 ± 0.28 | 129.67 ± 108.72 | 524.67 ± 23.25 |
| BIM-38039 | 1.48 ± 0.24 | 297.00 ± 52.60 | 3763.33 ± 728.28 |
| BIM-38012 | 2.57 ± 0.30 | 540.00 ± 432.24 | 369.00 ± 42.75 |
| BIM-38009 | 2.92 ± 0.69 | 14482.00 | 3258.33 ± 165.30 |
| BIM-38046 | 2.92 ± 1.12 | 72.65 ± 2.59 | 849.00 |
| BIM-38040 | 3.97 ± 0.67 | 1440.33 ± 368.08 | 1413.61 ± 201.26 |
| BIM-38013 | 4.01 ± 0.48 | 161.50 ± 450 | 192.00 ± 27.71 |
| BIM-38026 | 4.27 ± 0.46 | 225.00 ± 72.00 | 2755.00 ± 2246.00 |
| BIM-38023 | 4.73 ± 1.55 | 413.50 ± 215.50 | 5201.33 ± 2241.98 |

The following procedure was used to determine the ability of various opioid peptides to inhibit binding at opioid receptors. Crude membranes were prepared by homogenization of guinea-pig or rat forebrain samples in 20 ml of ice-cold 50 mM Tris-HCl with a Brinkman Polytron (setting 6, 15 sec.). Buffer was added to obtain a final volume of 40 ml, and the homogenate centrifuged in a Sorval SS-34 rotor at 39,000 g for 10 min. at 0°–4° C. The resulting supernatant was decanted and discarded. The pellet was rehomogenized in ice-cold buffer, pre-incubated at 37° C. for 45 min., diluted, and centrifuged as before. The final pellet was resuspended in 50 mM Tris HCl and held on ice for the receptor binding assay.

Aliquots of the washed membrane preparation (described above) were incubated in 50 mM Tris HCl at a total volume of 2.0 ml at 25° C. with an opioid receptor ligand (see below) and various concentrations of the unlabeled test compounds. Mu and kappa receptor assays were incubated for 60 minutes. Delta receptor assays were incubated for 40 minutes. At the end of the incubation periods, the assays were terminated by rapid filtration though Whatman GF/B glass fiber filters, and the bound radioactivity trapped on the filters counted by liquid scintillation spectrometry. For each of the three receptor subtypes, specific binding was calculated as the total radioligand bound minus that bound in the presence of 1000 nM levallorphan.

Three radiolabeled opioid receptor ligands, DAGO, DPPE, and U69,593, were used in μ receptor, δ receptor and κ receptor assays, respectively. The structures of the ligands are as follows.

DAGO: Tyr-D-Met-Gly-Me-Phe-NH-$CH_2$-$CH_2$-OH;

DPPE: Tyr-D-Peniciliamine-Gly-Phe-D-Peniciliamine (cyclized); and

U69,953: (5,7,8)-(−)-N-methyl-N-(7-(1-pyrrolidinyl)-1-oxaspiro-(4,5)dec-8-yl)-benzeneacetamide.

Inhibition constants ("Ki") were calculated from the equation Ki=$IC_{50}$/(1+L/Kd), where L is the radioligand concentration and Kd is the equilibrium dissociation constant for the radioligand. The $IC_{50}$ was derived from the inhibition data by linear least squares regression of log (B/Bt−B) versus log I, where I is the test compound concentration, Bt is the total amount of radioligand specifically bound, and B is the amount of specific binding in the presence of a given concentration of the unlabeled peptide. The $IC_{50}$ is the antilog of log I, when the expression, log (B/Bt−B) equals zero.

The structures of the test compounds are as follows.

BIM-38052: tyrosyl-D-arginyl-glycyl-APP amide

BIM-38031: tyrosyl-D-alanyl-glycyl-App amide

BIM-38020: tyrosyl-D-arginyl-glycyl-PEG amide

BIM-38007: tyrosyl-D-alanyl-glycyl-AHPPA amide

BIM-38039: tyrosyl-D-alanyl-glycyl-PEG-methionine amide

BIM-38012: tyrosyl-D-alanyl-glycyl-ACHPA amide

BIM-38009: tyrosyl-D-alanyl-glycyl-PEG amide

BIM-38046: tyrosyl-D-alanyl-glycyl-homophenylalanine amide

BIM-38040: tyrosyl-D-alanyl-glycyl-PEG methioninol

BIM-38013: tyrosyl-D-arginyl-glycyl-phenylalanyl-ψ-($CH_2NH$)-leucine amide

BIM-38026: tyrosyl-D-alanyl-glycyl-ψ($CH_2NH$)-phenylalanine propylamide

BIM-38023: tyrosyl-D-alanyl-glycyl-ψ($CH_2NH$)-phenylalanine ethylamide (2) Sodium ions discriminate opioid agonist/antagonist properties NaCl decreases the potency of opioid agonists (i.e., morphine) and has no effect on the potency of oipoid antagonists (i.e., naloxone). Several tested opioid peptides of the invention all showed some degree of agonist property, as evidenced by a decreased potency in the presence of NaCl. See Table 3 below.

TABLE 3

The Effect of Sodium Ion on the Binding to Mu Opiate Receptors In Vitro

| | Ki (nM) | | |
|---|---|---|---|
| | −NaCl | +NaCl* | −NaCl/+NaCl |
| BIM-38007 | 4.0 ± 0.6(3) | 13 ± 4.0(2) | 3.3 |
| BIM-38009 | 6.9 ± 3.6(3) | 68 ± 8.5(2) | 9.9 |
| BIM-38005 | 19 ± 3.6(5) | 145 ± 14(3) | 7.6 |
| Morphine | 3.6 | 140 | 39 |
| [D-Ala$^2$, D-Leu$^3$] enkephalin | 15 | 560 | 37 |
| naloxone | 0.9 | 0.7 | 0.8 |

*100 mM

The binding experiments described in Table 3 were performed as described above, except for the presence of 100 mM NaCl.

(3) In Vivo Growth Inhibition of Melanomas by Opioid Peptide

As shown in Table 4, administration of two opioid peptides (BIM-38007 and BIM-38009, see above for structures) inhibited the growth of B16-F10 melanomas in in vivo animal experiments. In these experiments, tumors were induced in BALB/c athymic nude mice. 50 μg of peptide in 0.2 ml of saline was injected subcutaneously twice a day on days 1–5, 6-days Subrenal Capsule Assay ("SRCA").

Control animals received 0.2 ml of saline subcutaneously twice daily on days 1–5. Mice were sacrificed on day 6 and tumor size determined by a microscope. The results are reported as the change in tumor size from day 0 (time of tumor implantation) to day 6 (time of assay termination).

TABLE 4

Effect of Opioid Peptides on Tumor Size B-16 Melanoma

| Group No. | Treatment | Change In Tumor Size (omu) | % T/C |
|---|---|---|---|
| 1 | Vehicle Treated Control | 21.3 ± 3.3 | — |
| 2 | BIM-38007 | 18.1 ± 2.0 | 85 |
| 3 | BIM-38009 | 14.7 ± 3.1 | 69 | omu = ocular micrometer unit, 1.0 mm = 10 omu;
% T/C = omu experimental/omu control Table 5 compares the antitumor activity of an opioid BIM-38009 versus methadone. A subcutaneous tumor assay was used in which xenografts of the human non-small cell lung cancer were implanted s.c. in athymic nude mice. Test compounds were administered s.c. or i.p., twice daily, from day 4 post tumor implantation to day 35. The results are reported as means±s.e.m. on 8 animals per group. For structure of BIM-38009, see above.

TABLE 5

Antitumor Activity of BIM-38009: Human NSLC A549

| Group No. | Treatment | Tumor Weight (mg) (Day 34) | & T/C |
|---|---|---|---|
| 1 | Saline Vehicle Treated control, 0.2 ml/inj., s.c., b.i.d, q.d. 4–35 | 305 ± 60 | — |
| 2* | BIM-38009, 500 μg/inj., s.c., b.i.d., q.d., 4–35 | 134 ± 36 | 44 |
| 3 | Methadone, 10 mg/kg/inj., i.p., q.d. 4–35 | 337 ± 57 | 110 |

*Significance of difference from control: p < 0.01

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A peptide of the formula:

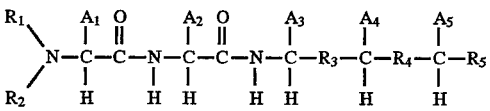

in which $A_1$ is the identifying group of an amino acid selected from 3,4-dihydroxyphenylalanine, 3,4-dimethoxyphenylalanine, azatyrosine, Tyr, and 2,6-dimethyltyrosine;

$A_2$ is the identifying group of an amino acid selected from D-Ala and D-Arg;

$A_3$ is H;

$A_4$ is H, cyclohexylmethyl, or the identifying group of an amino acid selected from 3,4-dihydroxyphenylalanine and 3,4-dimethoxyphenylalanine;

$A_5$ is the identifying group of a D- or L-amino acid selected from Leu, Nle, Lys, Met and Met(O), or is deleted together with $R_4$—CH attached thereto;

each $R_1$ and $R_2$ is —H, —C(NH$_2$)=NH, or C$_{1-12}$ alkyl;

$R_3$ is

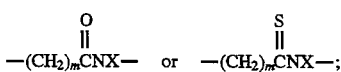

$R_4$ is

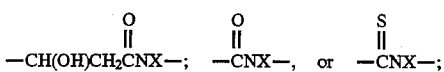

$R_5$ is —(CH$_2$)$_{n+1}$OH,

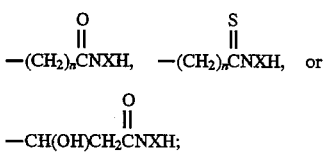

wherein m is 0–6, n is 0–6, and X is H, C$_{1-12}$ alkyl, C$_{6-12}$ aryl, C$_{7-18}$ aralkyl, C$_{7-18}$ alkaryl, C$_{6-17}$ pyridylalkyl, or C$_{6-17}$ alkylpyridyl; provided that when one of R$_1$ and $R_2$ is —C(NH$_2$)=NH, then the other must be H; or a pharmaceutically acceptable salt thereof.

2. The peptide of claim 1, wherein $A_1$ is the identifying group of an amino acid selected from 3,4-dihydroxyphenylalanine, 3,4-dimethoxyphenylalanine, and Tyr;

$A_5$ is the identifying group of a D- or L-amino acid selected from Leu, Met and Met(O), or is deleted together with $R_4$—CH attached thereto;

each $R_1$ and $R_2$ is —H or —C(NH$_2$)=NH;

$R_3$ is

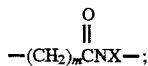

$R_4$ is

$R_5$ is —(CH$_2$)$_{n+1}$OH,

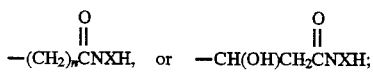

m is 0–2;

n is 0–2; and

X is H, $C_{1-12}$ alkyl, or $C_{7-18}$ aralkyl.

3. The peptide of claim 1 having the formula of:
tyrosyl-D-alanyl-glycyl-PEG-methionine amide,
tyrosyl-D-arginal-glycyl-PEG-methionine amide,
tyrosyl-D-alanyl-glycyl-PEG methioninol,
tyrosyl-D-arginyl-glycyl-PEG methioninol,
tyrosyl-D-alanyl-glycyl-ACHPA amide,
tyrosyl-D-arginyl-glycyl-ACHPA amide,
tyrosyl-D-alanyl-glycyl-PEG amide,
tyrosyl-D-arginyl-glycyl-PEG amide,
amidinotyrosyl-D-alanyl-glycyl-PEG amide,
amidinotyrosyl-D-arginyl-glycyl-PEG amide,
tyrosyl-D-alanyl-glycyl-DOPA amide, or
tyrosyl-D-arginyl-glycyl-DOPA amide.

4. The peptide of claim 3 having the formula of:
tyrosyl-D-alanyl-glycyl-PEG-methionine amide,
tyrosyl-D-arginal-glycyl-PEG-methionine amide,
tyrosyl-D-alanyl-glycyl-PEG methioninol,
tyrosyl-D-arginyl-glycyl-PEG methioninol,
tyrosyl-D-alanyl-glycyl-ACHPA amide,
tyrosyl-D-arginyl-glycyl-ACHPA amide,
tyrosyl-D-alanyl-glycyl-PEG amide, or
tyrosyl-D-arginyl-glycyl-PEG amide.

* * * * *